(12) United States Patent
Lavin

(10) Patent No.: US 6,380,255 B1
(45) Date of Patent: *Apr. 30, 2002

(54) TREATMENT FOR DERMAL SKIN ATROPHY USING THYROID HORMONE COMPOUNDS OR THYROID HORMONE-LIKE COMPOUNDS

(75) Inventor: Thomas N. Lavin, Watchung, NJ (US)

(73) Assignee: Karo Bio AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/617,052

(22) Filed: Jul. 14, 2000

Related U.S. Application Data

(63) Continuation-in-part of application No. 08/973,627, filed as application No. PCT/US96/09975 on Jun. 7, 1996, now Pat. No. 6,221,911, which is a continuation-in-part of application No. 08/481,698, filed on Jun. 7, 1995, now abandoned.

(51) Int. Cl.$^7$ ............................................. A61K 31/195
(52) U.S. Cl. ........................ 514/567; 514/369; 514/469; 514/557; 514/646
(58) Field of Search ................................ 514/567, 469, 514/369, 557, 646

(56) References Cited

U.S. PATENT DOCUMENTS

| | | | |
|---|---|---|---|
| 4,889,847 A | 12/1989 | Kligman et al. | 514/171 |
| 5,019,569 A | 5/1991 | Kligman et al. | 514/171 |
| 5,118,707 A | 6/1992 | Chatterjee et al. | 514/469 |
| 5,284,971 A | 2/1994 | Walker et al. | 562/429 |
| 5,869,470 A | 2/1999 | Blank et al. | 514/159 |
| 6,221,911 B1 * | 4/2001 | Lavin et al. | |

FOREIGN PATENT DOCUMENTS

| | | |
|---|---|---|
| BE | 515 812 A | 5/1953 |
| CH | 642 851 A | 5/1984 |
| EP | 0 060 776 A | 9/1982 |
| FR | 6 656 M | 1/1969 |
| FR | 2 153 202 A | 4/1973 |
| FR | 2 139 748 A | 12/1973 |
| FR | 2 357 246 A | 3/1978 |
| FR | 2 354 101 A | 6/1978 |
| GB | 782 745 A | 11/1957 |
| GB | 859 546 A | 1/1961 |
| GB | 1 354 263 A | 5/1974 |

OTHER PUBLICATIONS

"Concurrent application of tretinoin (retinoic acid) partially protects against corticosteroid–induced epidermal atrophy", McMichael et al., *British Journal of Dermatology*, vol. 135, pp. 60–64, 1996.

"Systemic glucocorticoids decrease the synthesis of type I and type III collagen in human skin in vivo, whereas isotretinoin treatment has little effect", *British Journal of Dermatology*, Autio et al., vol. 131, pp. 660–663, 1994.

"Laser Skin Resurfacing", Lowe et al., *Derm. Surg.*, vol. 21, pp. 1017–1019, 1995.

"Retinoic Acid and $CO_2$ Laser Resurfacing", McDonald et al., *Plastic and Reconstructive Surgery*, vol. 104, No. 7, pp. 2236–2238, 1999.

File Embase, Abstract AN: 84027313, Dec. 1983 US.
File Embase, Abstract AN:82189935, May 1982, Italy.
File Embase, Abstract AN:81038096, Jun. 1979, Italy.
File Embase, Abstract AN:74156248, Dec. 1973, Italy.
(Abstract) WPI,AN 82–004847, Feb. 1982, Romania.
DeRycker et al., "Effects of 3.5,3'–triiodothyronine on collagen synthesis by cultured human skin fibroblasts", FEBS Letters, No. 1, vol. 174, 1984, pp. 34–37.

\* cited by examiner

*Primary Examiner*—Minna Moezie
*Assistant Examiner*—Mojdeh Bahar
(74) *Attorney, Agent, or Firm*—Todd E. Garabedian; Wiggin & Dana

(57) ABSTRACT

The present invention is directed to a method for treating dermal atrophy of the skin. The method of the invention includes applying a composition to the skin of a mammal suffering from dermal atrophy of the skin, and comprising at least one thyroid hormone compound or thyroid hormone-like compound together with a pharmacologically acceptable base suitable for topical application, wherein the thyroid hormone compound or the thyroid hormone-like compound binds to TR-α or TR-β with an equilibrium dissociation constant, $K_d$, of at least $10^{-5}$ M. The invention is also directed to an article of manufacture comprising packaging material and a pharmaceutical agent contained within the packaging material, wherein the pharmaceutical agent is therapeutically effective for treating dermal atrophy of the skin.

22 Claims, 6 Drawing Sheets

TREATMENT FOR DERMAL SKIN ATROPHY USING THYROID HORMONE COMPOUNDS OR THYROID HORMONE-LIKE COMPOUNDS

CROSS-REFERENCE TO RELATED APPLICATIONS

This application is a Continuation-in-Part of U.S. Ser. No. 08/973,627 filed Mar. 9, 1998, issued as U.S. Pat. No. 6,221,911, which is a §371 filing from International Application No. PCT/US96/09975 filed Jun. 7, 1996, which is a CIP of U.S. Ser. No. 08/481,698 now abandoned filed Jun. 7, 1995.

BACKGROUND OF THE INVENTION

1. Field of the Invention

This invention relates to thyroid-hormone receptor binding compounds, and more particularly to thyroid-hormone receptor binding compounds useful as dermatologic treatments for atrophy of the dermis.

2. Brief Description of the Related Art

There are a considerable number of skin conditions and diseases which significantly affect the appearance of the skin. Examples of these skin conditions include stria, cellulite, roughened skin, actinic skin damage, intrinsically aged skin, photodamaged skin, lichen planus, ichtyosis acne, psoriasis, wrinkled skin, eczema, seborrheic dermatitis, scleroderma, hyperkeratinizing disorders, keloids and skin scarring.

A wide variety of medically useful topical skin preparations are currently commercially available to treat many of these skin conditions and diseases. A large number of these skin preparations include topical steroids such as glucocorticoids, and retinoid topical medicaments, both of which have varying side-effects and usefulness in many patients. Particularly, eczema and psoriasis are usually treated with topical steroids such as hydrocortisone, betamethasone, and clobetasol propionate. The side effects of topical steroid use, particularly in the long term are well known and include skin atrophy consisting of atrophy of both the dermis and epidermis, a risk for systemic absorption of the drug, and rebound phenomena when the drug is withdrawn.

Oral glucocorticoids also produce skin atrophy with chronic use. Therefore certain diseases and conditions which are treated with oral or inhaled glucocorticoids are associated with atrophy. For example, organ transplantation, asthma, rheumatic diseases, and renal diseases are often treated with oral glucocorticoids which results in skin atrophy.

Dermal skin atrophy results from reduced collagen in the dermis, decreased cellularity in the dermis, and reduces the depth of the dermis, resulting in increased fragility of the skin, transparency of the skin, and easy bruising (Talwar et al., J. Inv. Derm. 105:285 (1995); Uitto, H. Geriatric Dermatology 5:127 (1989)). Among the main causes of dermal skin atrophy are aging, photodamage, topical or systemic glucocorticoids, Cushing's disease, rheumatoid arthritis, and diabetes (see, Textbook of Dermatology, (1997); Gilchrist, B. A. Brit. J. Dermatology 135:867 (1996); Talwar et al., J. Inv. Derm. 105:285 (1995)).

Retinoic acid has been shown to partially ameliorate the condition of photoaging (Drugs and Aging 1:12–16 (1996)), but has not been fully successful in reversing steroid induced dermal skin atrophy in humans (Griffiths, Br. J. Dermatology 135:60–64 (1996)). Other medically useful treatments involve the use of alpha hydroxy acids as disclosed in U.S. Pat. Nos. 5,254,343; t,284,971; 5,401,772; 3,649,597; 3,357,887; 4,168,385; and 5,179097; and European Patent Application No. 580550. Currently, there are no treatments for dermal atrophy of the skin that are widely accepted by the medical community or can reverse glucocorticoid-induced dermal atrophy.

The structurally similar thyroid hormone compounds 3,3', 5-triiodo-L-thyronine (T3) and L-thyroxine ($T_4$) have a very wide range of effects. In adult mammals they influence nearly all organs, the metabolism of nutrients, basal metabolic rate, and oxygen consumption. In humans, the deficiency or excess of circulating thyroid hormone compounds results in the well characterized syndromes, hypo- and hyperthyroidism. Small concentrations of thyroid hormone metabolites which are also endocrinologically active exist. Among these compounds are tri-iodothyroacetic acid ("Triac" [4-(4-hydroxy-3-iodophenoxy)-3,5-diodophenyl] acetic acid) and tri-iodopropionic acid ("Tri-prop" [4-(4-hydroxy-3-iodophenoxy)-3,5-diiodophenyl)]propionic acid).

Thyroid hormone compounds exert many of their actions by binding to a family of receptor proteins termed the C-erb-A family. In humans, their receptor protein family is now known to comprise several members, notably the human thyroid receptor α-1, the human thyroid receptor α-2 which binds the hormone poorly or not at all, the human thyroid receptor β-1, and the human thyroid receptor β-2. These proteins are part of a larger superfamily of steroid hormone receptors which comprises the glucocorticoid receptors, the retinoic acid receptors, the vitamin D receptors, and the insect molting receptors (e.g., the receptors for ecdysone and the insect juvenile hormones). Receptors for hormone compounds are found in human skin, human fibroblasts and keratinocytes and they are also found in many other tissues within the human body, In addition to the naturally occurring thyroid hormone compounds (e.g., triiodothyronine and tetraiodothyronine), a large number of chemical compounds which bind to the thyroid hormone receptor and which produce thyroid hormone-like effects have been synthesized (see, for example, U.S. Pat. No. 5,401,772).

Thyroid hormone compounds, in many cases, act indirectly by influencing the effects of other hormones and tissues. For example in the rat, thyroid administration increases pituitary growth hormone production which in turn affects hepatic protein production including that of alpha-2 euglobulin. Functionally, in the rat, growth hormone may act as a second message for thyroid hormone. The biology of thyroid hormone compounds has been extensively studied only after oral administration, which makes the relationship between a direct effect of thyroid hormone compounds and an indirect effect mediated by thyroid hormone modulation of other autocrine, paracrine or endocrine factors difficult to ascertain.

Orally administered thyroid hormones influence the connective tissue biology of the skin. When given orally, thyroid hormones induce an increase in neutral salt and acid soluble collagen, but decrease insoluble collagen in the skin of guinea pigs (Drozdzm, M. et al., Endokrinologie 73:105–111, 1979). In cell culture, fibronectin production is decreased in human fibroblasts and fibroblast glycosaminoglycans are either decreased or unchanged depending on the experimental conditions used (Murata, Y. et al., J. Clin. Endocrinol. Metab. 64:334–339, 1987; Watxke, H. et al., Thrombosis Res. 46:347–353, 1987; Murata, Y. et al., JCEM 57:1233–1239, 1983; Ceccarelli, Pl, et al., JCEM 65:242–246, 1987). Keratin gene expression for both the basal cell keratin K5 and K14 genes and the differentiation-specific K10 gene is negatively regulated by thyroid hormones (Tomic-Canic, M. et al., J. Invest. Dermatol. 99:842–847, 1992; Blumenberg, M. et al., J. Invest. Dermatol. 98:42S–49S, 1992) Thyroid hormone added to fibroblasts in culture decreases collagen production (De Ryker, FEBS Lett. 174:34–37 (1984)). Some of these effects are mirrored by similar cell culture responses to retinoic acid or the retinoid Tretinoin.

Histological studies of skin from individuals who have the medical condition hyperthyroidism show an increased number of cell layers in the skin, reflected by mean epidermal cell number, increased protein turnover with increased proline incorporation and generalized increases in epidermal proliferation compared to normal skin (Holt, P. J. A. et al., Br. J. Dermatol. 95:513–518, 1976). In human clinical biology, thyroid hormone excess leads to a general smoothing of the skin and the loss of wrinkles especially over the olecranon (elbow) surface.

Orally given thyroid hormone compounds in excess of normal bodily requirements or medical conditions which are associated with excess thyroid hormone compounds such as Grave's disease or toxic nodular goiter produce an acceleration of heart beat with associated heart failure, cardiac arrhythmias, osteoporosis, increased intestinal motility leading to diarrhoea, psychiatric abnormalities, and an increase in the basal metabolic rate. Attempts to use oral thyroid hormone compounds for diminishing lipid levels in man resulted in increased cardiac deaths.

What is needed in the art is a method of treating dermal skin atrophy that does not suffer the drawbacks of current treatment used in the art. The present invention is believed to be an answer to that need.

SUMMARY OF THE INVENTION

In one aspect, the present invention is directed to a method for treating dermal atrophy of the skin, comprising the step of applying a composition to the skin of a mammal suffering from dermal atrophy of the skin, the composition comprising at least one thyroid hormone compound or thyroid hormone-like compound together with a pharmacologically acceptable base suitable for topical application, wherein the thyroid hormone compound or the thyroid hormone-like compound binds to TR-α or TR-β with an equilibrium dissociation constant, $K_d$, of at least $10^{-5}$ M, wherein $K_d=(R) \cdot (L)/(RL)$, where (R) is the concentration of receptor, (L) is the concentration of ligand, and (RL) is the concentration of the receptor-ligand complex, and wherein the dermal atrophy of the skin is reduced.

In another aspect, the present invention is directed to an article of manufacture comprising packaging material and a pharmaceutical agent contained within the packaging material, wherein the pharmaceutical agent is therapeutically effective for treating dermal atrophy of the skin, and wherein the packaging material comprises a label which indicates that the pharmaceutical agent can be used for treating dermal atrophy of the skin, and wherein the pharmaceutical agent comprises at least one thyroid hormone compound or thyroid hormone-like compound in a pharmacologically acceptable base suitable for topical application, wherein the thyroid hormone compound or the thyroid hormone-like compound binds to TR-α or TR-β with an equilibrium dissociation constant, $K_d$, of at least $10^{-5}$ M wherein $K_d=(R) \cdot (L)/(RL)$, where (R) is the concentration of receptor, (L) is the concentration of ligand, and (RL) is the concentration of the receptor-ligand complex.

In yet another aspect, the present invention is directed to a composition for treating dermal atrophy of the skin, comprising: at least one thyroid hormone compound or thyroid hormone-like compound selected from the group consisting of tri-iodothyroacetic acid, tri-iodopropionic acid, 4-[2,6-dibromo-4-(1H-tetrazol-5-ylmethyl)-phenoxyl-2-isopropyl-phenol, 4-(4-hydroxymehyl-2,6-diiodophenoxy)-2-iodo-phenol, and combinations thereof; and a pharmacologically acceptable base comprising oil in water emulsions, water in oil emulsions, sprays, liposomes, creams, lotions, solutions, and combinations thereof.

In yet another aspect, the present invention is directed to a method of improving healing of wounded skin of a patient, comprising the step of applying a composition to the wounded skin of the patient, the composition comprising at least one thyroid hormone compound or thyroid hormone-like compound together with a pharmacologically acceptable base suitable for topical application, wherein the thyroid hormone compound or the thyroid hormone-like compound binds to TR-α or TR-β with an equilibrium dissociation constant, $K_d$, of at least $10^{-5}$ M, wherein $K_d=(R) \cdot (L)/(RL)$, where (R) is the concentration of receptor, (L) is the concentration of ligand, and (RL) is the concentration of the receptor-ligand complex, and wherein the healing of the wounded skin is improved.

In another aspect, the present invention is directed to a method of dermatological surgical pretreatment of a patient with atrophied skin, comprising the step of applying a composition to the atrophied skin of the patient prior to dermatological surgery, the composition comprising at least one thyroid hormone compound or thyroid hormone- like compound together with a pharmacologically acceptable base suitable for topical application, wherein the thyroid hormone compound or the thyroid hormone-like compound binds to TR-α or TR-β with an equilibrium dissociation constant, $K_d$, of at least $10^{-5}$ M, wherein $K_d=(R) \cdot (L)/(RL)$, where (R) is the concentration of receptor, (L) is the concentration of ligand, and (RL) is the concentration of the receptor-ligand complex.

These and other aspects will become apparent from the following drawings and detailed description.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
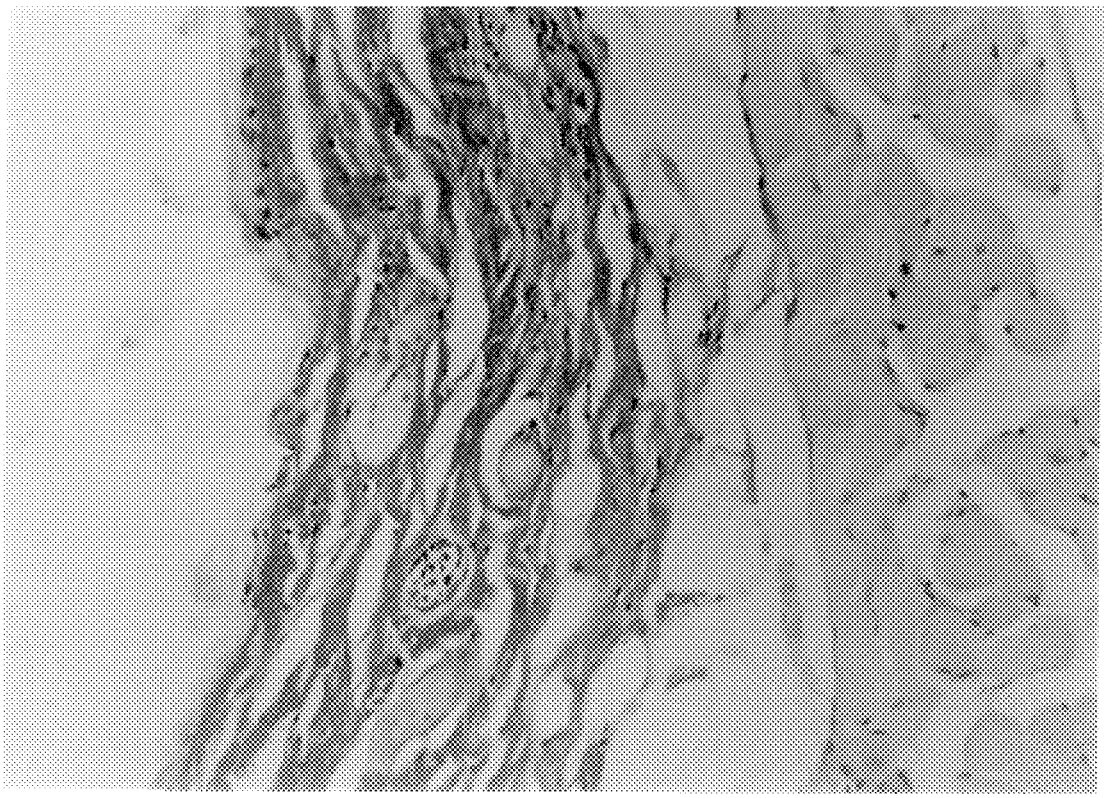
FIG. 1 is a biopsy micrograph analysis (200× magnification) of mouse skin treated with betamethasone and visualized with van Gieson, and/or hematoxylin/eosin stains.

Agents which improve the structure and integrity of the dermis are not well known. It has now been found that topical application of a composition comprising at least one thyroid hormone compound or thyroid hormone-like compound in a pharmacologically acceptable base is effective in treating dermal atrophy of the skin. Thyroid hormone compounds or thyroid hormone-like compounds have also been found to diminish easy bruising of the skin resulting from surgical procedures and from everyday injury. They also provide an improved cosmetic appearance to aging, atrophied, steroid-affected, or sun damaged skin which exhibits fragility, transparency, mottling, and appearance of capillaries. They also reverse and prevent the dermal atrophy induced by glucocorticoids and corticosteroids. These conditions are improved or reversed, according to the method of the invention, by application of the above topical composition Medical textbooks define thyroids as those hormones that circulate in the human body, namely T-3 (Tri-iodothyronine, 3,5,3'-triiodothyronine and T-4 (D and L thyroxine) and their metabolites. However, it s now clear that many compounds which possess thyroid hormone activity may have considerably different chemical structure, including for example the loss of an amino acid group or the elimination of iodine from the molecule. Accordingly, for the purposes of this invention a "thyroid hormone compound" or "thyroid hormone-like compound", which terms are used interchangeably herein, is any chemical entity, including peptides, which binds to thyroid hormone receptor TR-α or β with a dissociation constant, $K_d$, of at least $10^{-5}$ Molar (Goodman and Gilman, The Pharmacologic Basis of Therapeutics, p. 30, 1975) when measured by any of the methods known in the art. Furthermore, the thyroid hormone receptor binding drug should be active when applied topically at a concentration no higher than 0.1 Molar. Such ligands may be considered agonists when they have similar agonistic effects as the natural hormone or may be considered antagonists when the compounds antagonize the effects of the natural hormone compounds. Partial agonist/antagonists also may exist. Suitable ligands may be agonists or antagonists. The thyroids may be any natural or synthetic analog of triiodothyroacetic acid ("Triac") which binds to the thyroid hormone receptor within the above range of $K_d$ and possesses the biological activity of triiodothyroacetic acid.

For the purposes of this invention, the term thyroid hormone receptor will include all of the gene products of C-erb-A and its variants which bind thyroid hormone compounds or thyroid hormone-like compounds. Additionally, the terms steroids, glucocorticoids, and corticosteroids are used interchangeably for the dermatological purposes described herein.

As indicated above, the present invention is directed to a method for treating, reversing, or preventing dermal skin atrophy. The method of the present invention comprises the step of apply a composition to the skin of a mammal suffering from dermal atrophy of the skin, the composition comprising at least one thyroid hormone compound or thyroid hormone-like compound together with a pharmacologically acceptable base suitable for topical application, wherein the thyroid hormone compound or the thyroid hormone-like compound binds to TR-α or TR-β with an equilibrium dissociation constant, $K_d$, of at least $10^{-5}$ M, wherein $K_d=(R)\cdot(L)/(RL)$, where (R) is the concentration of receptor, (L) is the concentration of ligand, and (RL) is the concentration of the receptor-ligand complex, and wherein the dermal atrophy of the skin is reduced. The present invention is also directed to an article of manufacture comprising packaging material and a pharmaceutical agent contained within said packaging material. The pharmaceutical agent is therapeutically effective for treating dermal atrophy of the skin, and comprises at least one thyroid hormone compound or thyroid hormone-like compound in a pharmacologically acceptable base suitable for topical application, wherein said thyroid hormone compound or said thyroid hormone-like compound binds to TR-α or TR-β with an equilibrium dissociation constant, $K_d$, of at least $10^{-5}$ M. The packaging material comprises a label which indicates that the pharmaceutical agent can be used for treating dermal atrophy of the skin.

The thyroid hormone compound or thyroid hormone-like compound may be any compound that meets the above definition. Suitable thyroid hormone or thyroid hormone-like compounds include Tri-iodothyronine (3,5,3'-triiodothyronine, T3); D and L thyroxine (T4); 3,3'5'triiodothyronine (reverse T3); 3,3'-diiodothyronine; T3 and T4 analogues such as 3,5,3',-Triiodo-L-thyronine methyl ester; 3,5,3'-Triiodo-L-thyronine hydrochloride; L-thyroxine hydrochloride; Tetrac (3-[4-(4-hydroxy-3,5-diiodophenoxy)-3,5-diiodophenyl]acetic acid); Triac ([4-(4-hydroxy-3-iodophenoxy)-3,5-diiodophenyl]acetic acid); Tetraprop; Triprop ([4-(4-hydroxy-3-iodophenoxy)-3,5-diiodophenyl]propionic acid); T4Bu; T3Bu; Thyroxamine; Triiodothyronamine; (5-Benzyloxy-2-methoxyphenyl)-(2-methoxypyrimidin-5-yl)-methanol; Benzyloxy-2-methoxyphenyl)-(6-methylpyridin-3-yl)methanol; (5-Benzyloxy-2-methoxyphenyl)-(5-bromo-2-methoxypyridin-4-yl)methanol; (5-benzyloxy-2-methoxyphenyl)-(2,6-difluoropyridin-3-yl)methanol; (5-Benzyloxy-2-methoxyphenyl)-(2-methoxypyridin-4-yl) methanol; 4-Methoxy-3-[(2-methoxypyrimidin-5-yl) methyl]phenol; 4-Methoxy-3-[6-methylpyrid-3-yl)methyl] phenol; 5-Benzyloxy-2-methoxybenzyl Bromide; (5-Benzyloxy-2-methoxyphenyl-(6-chloropyridazin-3-yl)-acetonitrile; 4-Benzyloxy-2-[2-methoxythiazol-5-yl) methyl]anisole; 6-[(5-Hydroxy-2-methoxyphenyl)methyl] thiazol-2-(3H); 3'-Heteroarylmethyl-4'-)-methyl-3,5-dinitro-N-trifluoro-acetyl-L-thyronine ethyl esters; 3'-heteroarylmethyl-3,5-di-iodo-4')-methyl-N-trifluoro-acetyl-L-thyronine Ethyl Esters; 3'-heteroarylmethyl analogues of 3,3',5-tri-iodo-L-thyronine (T3); 3'-substituted derivatives of the thyroid hormone 3,3'5-triiodo-L-thyronine (T3); L-3,3'-T2; DL-Br2I; L-Br2IPr; L-Me2I; L-Me3; L-Me4; L-Me2IPr; DL-IMeI; L-3,5-Dimethyl-3'-isopropylthyronine (DIMIT); DL-BPT4; B-triac; BP-tetrac; DL-SBT3; DL-SBT4; DL-MBT3; MB-tetrac; T2F; T2Cl; T2Br; T2Me; T2Et; T2iPr; T2nPr; T2sBu; T2tBu; T2iBu; T2Phe; T2F2; T2Cl2; T2Me2; 3,5,3'-Triiodo-D-thyronine; 3,5-Diiodo-4-hydroxyphenylpropionic acid (DIHPA); Aryloxamic acids; (arylamino)acetic acids; arylpropionic acids; arylthioacetic acids; (aryloxy)acetic acid; 3,3'-T2; 3,5-T2;

3',5'-T2; α-methyl-3,5,3'-triiodothyroacetic acid, α-methyl-3,5,3'-triiodothyropropionic acid, and α-methyl-3,5,3',5'-tetraiodothyropropionic acid; methylene- and carbonyl-bridged analogs of iodinated thyronines or thyroacetic acids or iodinated benzofurans; 3,5-diiodo-4-(2-N,N-diethylaminoethoxy)phenyl-(2-butylbenzofur-3-yl) methanol hydrochloride; 2-methyl-3-(3,5-diiodo-4-(2-N,N-diethylamino-ethoxy)-benzoyl)benzofuran hydrochloride; 2-n-butyl-3-(3,5-diiodo-4-carboxymethoxy-benzoyl) benzofuran; 2-methyl-3-(3,5-diiodo-4-hydroxy-benzoyl) benzofuran; 2-methyl-3-(3, 5-diiodo-4-carboymethoxy-benzyl) benzofuran; [4'-hydroxy-3'-iodo-3,5 diiodo-4-(2-N,N-dimethylamino-ethoxy)benzophenone hydrochloride; 2-butyl-3-(3-iodo-4-hydroxybenzoyl)benzofuran; 4',4-dihydroxy 3'3,5-triiodo-diphenylmethane; 3,5-diiodo-4-(2-N,N-diethylaminoethoxy)phenyl-(2-butylbenzofur-3-yl) methanol hydrochloride; 2-methyl-3-(3,5-diiodo-4-(2-N,N-diethylamino-ethoxy)-benzoyl)benzofuran hydrochloride; 2-n-butyl-3-(3'5-diiodo-4-carboxymethoxy-benzoyl) benzofuran; 2-methyl-3-(3,5-diiodo-4-hydroxy-benzoyl) benzofuran; 2-methyl-3-(3,5-diiodo-4-carboxymethoxy-benzyl)benzofuran; 4'1-hydroxy-3'-iodo-3,5-diiodo-4-(2-N,N-dimethylamino-ethoxy)benzophenone hydrochloride; 2-butyl-3-(3-iodo-4-hydroxybenzoyl)benzofuran; 4',4-dihydroxy-3'3,5-triiodo-diphenylmethane; 3,5-diethyl,3'-isopropyl thyronine (DIET); and IpTA2 (3,5 diiodo-3'isopropyl thyroacetic acid) and pharmacologically acceptable salts and derivatives thereof.

Other suitable thyroid hormone-like compounds are disclosed for example in U.S. Pat. Nos. 5,284,971; 3,649,679; 3,357,887; 4,168,385; 5,179,097, EP 0580550, EP 018351 and H. A. Selenkow and S. P. Asper, Jr., Physiol. Rev. 35 426 (1955); C. S. Pitman and J. A. Pitman in Handbook of Physiology, Section 7: Endocrinology, Vol. 3, R. O. Greep and E. B. Astwood, Eds., Thyroid American Physiological Society, Washington, D.C., 1974, p. 233; E. C. Jorgensen, Pharm. Ther. B, 2, 661 (1976); and E. C. Jorgensen, "Thyroid Hormones and Analogs. II. Structure-Activity Relationships," in Hormonal Proteins and Peptides, Vol. 6, Thyroid Hormones, C. H. Li, Ed., Academic, New York, 1978, p. 108., all of which are incorporated by reference herein. The choice of other suitable thyroid hormone-like compounds for use in the compositions and methods of the present invention is within the scope of the skilled worker.

The thyroid hormone compound or thyroid hormone-like compound is preferably in pure form, i.e., not contaminated with other compounds greater than about 0.1%.

The thyroid hormone compound or thyroid hormone-like compound is preferably at least partially dissolved in a solvent. The solvent is preferably an organic solvent selected from alcohol and alcohol and water solutions. More preferably, the organic solvent is selected from isopropanol, isopropanol and water, ethanol, and ethanol and water solutions containing at least 20% alcohol.

As described above, the thyroid hormone compound or thyroid hormone-like compound is mixed with a pharmacologically acceptable base that is suitable for topical application. Examples of suitable pharmacologically acceptable bases include oil in water (or water in oil) emulsions, sprays, liposomes, creams, lotions, solutions, and combinations thereof. The composition may also include suitable epidermal penetration-enhancing agents. The pharmacologically acceptable base is preferably an oil in water emulsion, a cream, or an alcoholic solution with glycerol. One particularly preferred pharmacologically acceptable base composition is a cream that includes linoleic, oleic, palmitic, and linolenic fatty acids or esters thereof and/or combined with triglycerides. This composition is r preferably combined with one or more additional substituents including glyceryl stearate, safflower oil, sorbitol, cetyl alcohol, stearic acid, triethanolamine, and the like.

Preferably, the composition comprises less than about 200 mg/100 ml, more preferably less than about 50 mg/100 ml of the thyroid hormone compound or thyroid hormone-like compound. Preferably the composition comprises a concentration $5 \times 10^8$ times or less the receptor dissociation constant, $K_d$, of the said at least one thyroid hormone compound or thyroid hormone-like compound. Preferably the composition is used to supply an effective amount of the thyroid hormone compound or thyroid hormone-like compound which generally ranges from 500 mg/m$^2$ to 0.1 mg/m$^2$ in one or more applications, preferably 250 mg/m$^2$ to 1 mg/m$^2$ per day in one or more applications. A useful amount to apply is 100 $\mu$l –1000 $\mu$l at the above concentrations. As will be appreciated by those skilled in the art, the effective concentration of the thyroid hormone compound or thyroid hormone-like compound will depend on factors such as metabolism of the compound, the pharmaceutical or cosmetic base employed, and the like.

The composition of the invention may also include other additional ingredients such as Vitamin D, estrogens, glucocorticoids and retinoids or analogues thereof to potentiate and modify the effects of the thyroid hormone compound or thyroid hormone-like compound for increased benefit. The composition may also include BHT (butylated hydroxy toluene) or BHA (butylated hydroxy anisole) as a hindered phenol to decrease iodine decomposition or oxidation. Furthermore, the composition may include compounds which facilitate passage of the thyroid hormone through the skin and compounds which act as sunscreens such as PABA. Preferably, the composition also includes a suitable antioxidant such as Tinuvin P or vitamin E. The choice of such compounds is within the scope of the skilled addressee. See for example Hermens W. A. J. J Pharmaceutisch Weekblad Scientific Edition 14(4A) 1992. Preferably, the thyroid hormone compound or thyroid hormone-like compound is not halogenated as such compounds are less prone to photodecomposition.

The composition used in the method of the invention is preferably applied to the skin of a mammal suffering from dermal atrophy of the skin, and more preferably to the skin of a human suffering from dermal atrophy of the skin. Preferably, the composition is applied from twice a day to every three days.

Topical administration of thyroid hormone to the skin allows direct thyroid hormone to modulation of the skin without influence by modulating factors produced in the pituitary, liver, or other organs. Further, the extensive metabolism by the liver and kidney of thyroid hormones into inactive metabolites is avoided by topical application. However, the dermatological effect of topically applied thyroid hormones in humans and animals is for the most part entirely unknown, and no medical publications appear which relate to this topic.

The topically-applied thyroid hormone compounds, or thyroid hormone-like compounds, used in the compositions and methods of the present invention are advantageous in that they enable the use of these chemical compounds to treat dermal skin atrophy, to improve the appearance of the skin, or normalize the physiology of the skin under pathophysiologic conditions without causing the undue adverse effects of orally administered thyroid hormone compounds, and avoids renal and hepatic metabolism of the thyroid hormone receptor binding chemical entity. In particular, the method of delivery of the thyroid hormone compounds and thyroid hormone-like compounds avoids liver and kidney metabolism of the hormones, blood circulation of the hormones to other tissue and binding to blood carrier proteins which can alter efficacy. Moreover, topical administration of the composition of the invention should not cause a hyperthyroid state.

The compositions and methods of the present invention are also useful for improving healing of wounded skin of a patient, as shown in detail in Example 2 below. The compositions and methods of the present invention are also useful for pretreatment a patient's atrophied skin prior to dermatologic surgery. It has been found that application of the composition of the present invention to the skin prior to dermatologic surgery results in faster healing of the skin in the weeks following the surgery. While not wishing to be bound by any particular theory, it is thought that the topically-applied thyroid hormone compounds or thyroid hormone-like compounds treat dermal skin atrophy by increasing the cellularity and thickness of the dermis and by an associated increase in collagen fibers, among other biological substances.

EXAMPLES

The invention is further described by the following Examples, but is not intended to be limited by the Examples. All parts and percentages are by weight and all temperatures are in degrees Celsius unless explicitly stated otherwise.

Example 1
Prevention of Glucocorticoid-Induced Atrophy in Normal Mice

Figure 2:
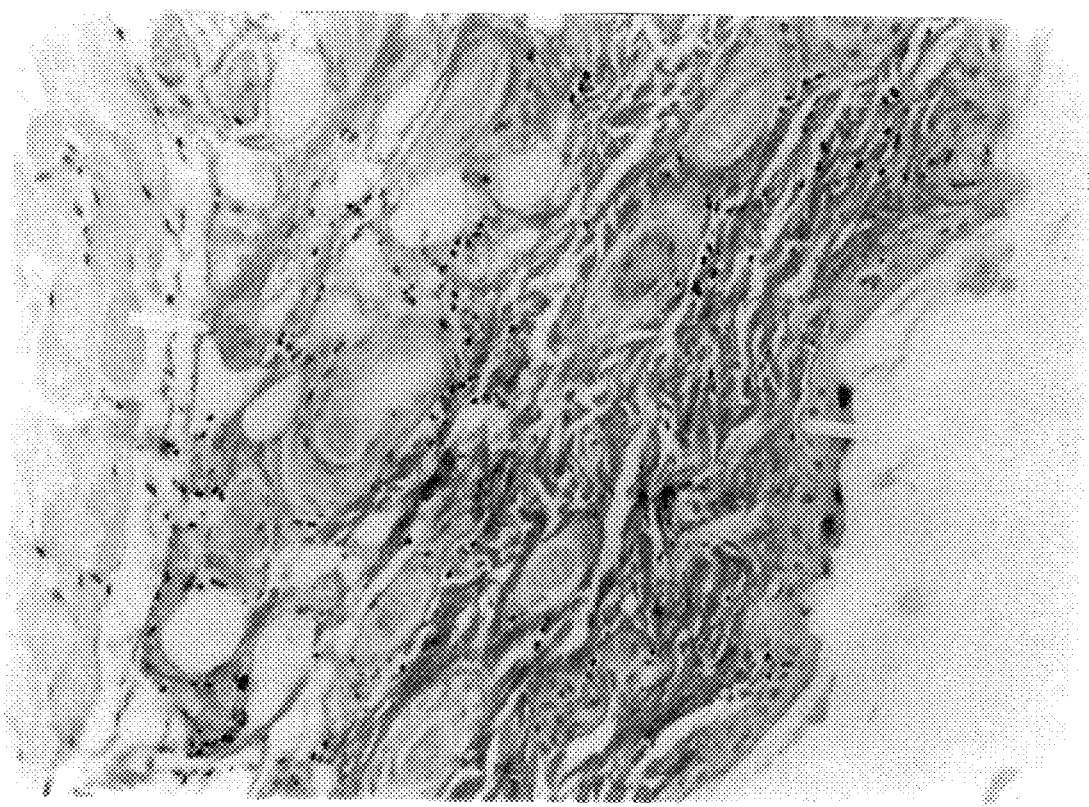
FIG. 2 is a biopsy micrograph analysis (200× magnification) of mouse skin treated with betamethasone plus 0.8 mM Triac and visualized with van Gieson, and/or hematoxylin/eosin stains.
Figure 3:
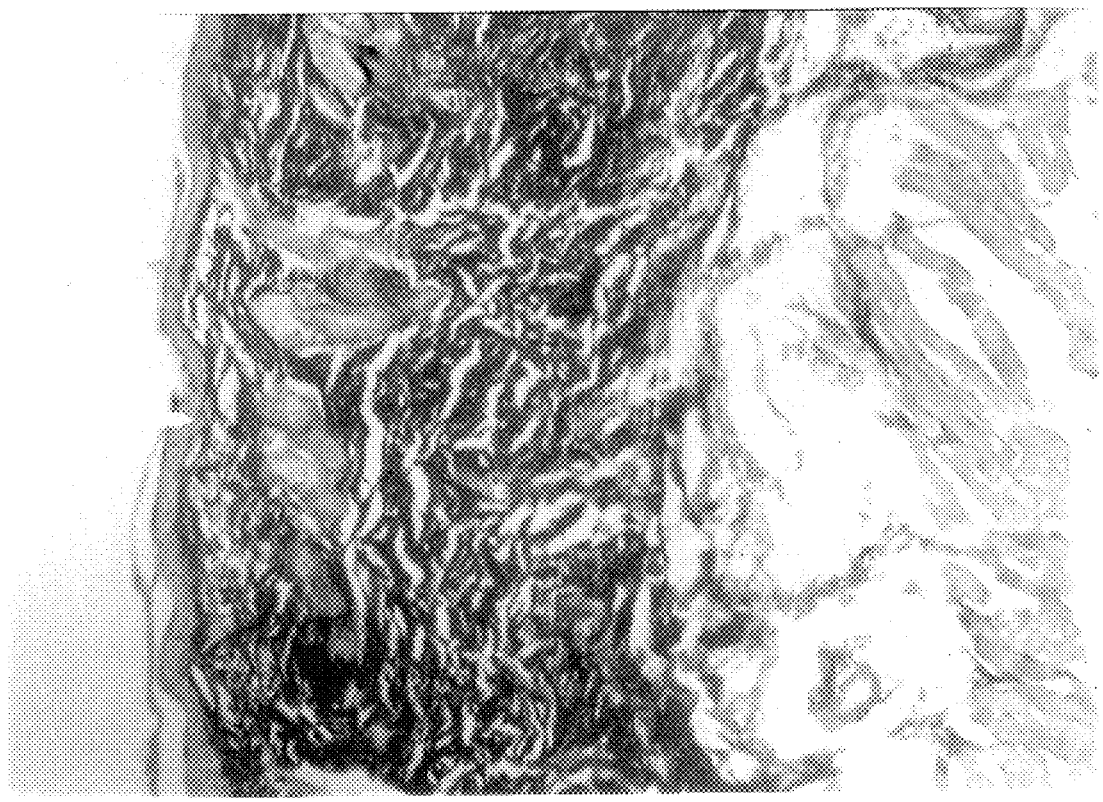
FIG. 3 is biopsy micrograph analysis (100×magnification) of treatment of mouse skin with Triac and visualized with van Gieson, and/or hematoxylin/eosin stains.

Normal Balb/c mice were used for the experiments. 100 µl solution of either betamethasone (0.2 mM in 50% isopropanol/water), topical thyroid agonist (Triac, Triprop, 4-[2,6-dibromo-4-(1H-tetrazol-5-ylmethyl)-phenoxy]-2-isopropyl-phenol (KB-067), 4-(4-hydroxymethyl-2,6-diiodophenoxy)-2-iodo-phenol (KB-026) in 50% isopropanol/water at various concentrations, or both were applied daily to the shaved back of the animals for one week. Biopsies were taken and the thickness of the dermal layer was measured microscopically after staining of collagen with Van Gieson stain. Five mice were used for each measurement at each concentration of test material and 5 sections were averaged from each mouse. Therefore each averaged measurement represents 25 determinations. FIGS. 1–3 and Tables 1 and 2 show the effects of a range of doses of Triac or Triac cream in preventing betamethasone-induced atrophy after one week.

In FIGS. 1–3, the arrows show the dermal layer which is predominantly collagen fibers. In some of the Experiments, Triac was formulated as a 0.1% or 0.03% cream and 100 µl was applied to the mice.

FIG. 1 shows a biopsy micrograph analysis (200× magnification) of mouse skin treated with betamethasone alone for one week, which is known to cause dermal skin atrophy. As shown in FIG. 1, the dermis appears to be very thinned, and some of the deep dermis has pulled away from the fat and muscle layer of the subcutaneaous tissues (a biopsy fixation artifact).

FIG. 2 shows a biopsy micrograph analysis (200× magnification) of mouse skin treated with 0.2 mM betamethasone plus 0.8 mM Triac, both in 50% isopropanol/water for one week. As shown in FIG. 2, the collagen layer (dermis) is almost double the thickness of the skin treated with betamethasone alone shown in FIG. 1. Thus, the Triac appears to be preventing betamethasone-induced dermal skin atrophy.

FIG. 3 shows a biopsy micrograph analysis (100× magnification) of treatment of mouse skin with Triac alone for one week. As shown in FIG. 3, the dermis is very dense and thicker than that shown in FIG. 2. Compared to normal mouse skin, the collagen layers are very thick and dense. Additionally, as shown in Table 2 below, Triac treated skin increased from 0.54 mm to 0.79 mm in a mouse treated with isopropanol/water alone. Therefore, Triac by itself can improve skin thickness in the absence of betamethasone-induced atrophy.

TABLE 1

Effect of Various Concentrations of TriAc on Corticosteroid-Induced Skin Atrophy in a Mouse Model

| Group | Thickness of dermis (mm) in 5 low power fields (×10) | | | | | mean (mm) | SD | no of mice | *p |
|---|---|---|---|---|---|---|---|---|---|
| Betamethasone 0.2 mM | 0.38 | 0.37 | 0.36 | 0.40 | 0.35 | 0.37 | 0.01 | 5 | |
| Bet. + 0.0008 mM TriAc | 0.40 | 0.40 | 0.36 | 0.38 | 0.36 | 0.38 | 0.02 | 4 | |
| Bet. + 0.008 mM TriAc | 0.40 | 0.47 | 0.48 | 0.44 | 0.46 | 0.45 | 0.02 | 5 | |
| Bet. + 0.08 mM TriAc | 0.50 | 0.48 | 0.53 | 0.49 | 0.50 | 0.50 | 0.02 | 5 | <0.05 |
| Bet. + 0.8 mM TriAc | 0.49 | 0.54 | 0.51 | 0.48 | 0.48 | 0.50 | 0.02 | 5 | <0.05 |
| Bet. + 8 mM TriAc | 0.52 | 0.50 | 0.47 | 0.52 | 0.49 | 0.50 | 0.02 | 5 | <0.05 |
| Vehicle (50% isopropanol/water) | 0.53 | 0.45 | 0.52 | 0.51 | 0.49 | 0.50 | 0.01 | 5 | <0.05 |

TABLE 2

Effect of Various Concentrations of TriAc and TriAc Cream on Betamethasone-induced Skin Atrophy in a Mouse Model

| Group | Thickness of dermis (mm) in 5 low power fields (×10) | | | | | mean (mm) | SD | no of mice | *p |
|---|---|---|---|---|---|---|---|---|---|
| Betamethasone 0.2 mM | 0.39 | 0.41 | 0.37 | 0.37 | 0.4 | 0.39 | 0.02 | 5 | |
| Bet. + TriAc 0.0008 mM | 0.4 | 0.37 | 0.4 | 0.43 | 0.4 | 0.40 | 0.02 | 4 | |
| Bet. + TriAc 0.008 mM | 0.41 | 0.37 | 0.4 | 0.43 | 0.4 | 0.40 | 0.02 | 5 | |
| Bet. + TriAc 0.08 mM | 0.52 | 0.53 | 0.45 | 0.5 | 0.52 | 0.50 | 0.03 | 5 | <0.05 |

TABLE 2-continued

Effect of Various Concentrations of TriAc and TriAc Cream on Betamethasone-induced Skin Atrophy in a Mouse Model

| Group | Thickness of dermis (mm) in 5 low power fields (×10) | | | | | mean (mm) | SD | no of mice | *p |
|---|---|---|---|---|---|---|---|---|---|
| Bet. + TriAc 0.8 mM | 0.54 | 0.6 | 0.6 | 0.56 | 0.62 | 0.58 | 0.03 | 5 | <0.05 |
| TriAc 0.8 mM | 0.72 | 0.82 | 0.84 | 0.76 | 0.82 | 0.79 | 0.05 | 5 | <0.05 |
| Bet. + placebo cr. | 0.35 | 0.4 | 0.37 | 0.39 | 0.4 | 0.38 | 0.02 | 5 | |
| Bet. + TriAc cr. (0.01 % TriAc) | 0.46 | 0.48 | 0.5 | 0.49 | 0.5 | 0.49 | 0.02 | 5 | <0.05 |
| Bet. + TriAc cr. (0.03 % TriAc) | 0.5 | 0.58 | 0.56 | 0.55 | 0.58 | 0.55 | 0.03 | 5 | <0.05 |
| Vehicle (50 % propanol/water) | 0.6 | 0.58 | 0.57 | 0.59 | 0.58 | 0.58 | 0.01 | 4 | <0.05 |

*p is defined as the probability that the result is due to chance alone.
"cr." = hydrophilic cream As can be seen in Tables 1 and 2, a gradual increase in effectiveness occurs as the concentration of Triac increases from 0.0008 to 8 mM, with the effect saturating at approximately 0.8 mM.

Table 3 shows the effects of Triac alone, Triac cream, TriProp, 4-[2,6-dibromo-4-(1H-terazol-5-ylmethyl)-phenoxyl]-2-isopropyl-phenol, 4-(4-hydroxymethyl-2,6-diiodophenoxy)-2-iodo-phenol on betamethasone-induced skin atrophy in a mouse model.

conclude that topical thyroids including tri-iodothryoacetic acid (triac) and others are effective at preventing glucocorticoid-induced dermal skin atrophy in mice.

Example 2

Treatment of Glucocorticoid-Induced Atrophy in Human

A 78-year old volunteer displayed tissue paper thin transparent skin, with atrophy of the dermis and subcutaneous fat, and easy bruisability. The patient had a history of rheumatoid arthritis treated with oral prednisone, but was currently

TABLE 3

Effect of Various Concentrations of TriAc cream, TroProp, 4-[2,6-dibromo-4-(1H-tetrazol-5-ylmethyl)-phenoxy]-2-isopropyl-phenol (KB-067), 4-(4-hydroxymethyl-2,6-diiodophenoxy)-2-iodo-phenol (KB-026) on Betamethasone-Induced Skin Atrophy in a Mouse Model

| Group | Thickness of dermis (mm) in 5 low power fields (×10) | | | | | mean (mm) | SD | no of mice | *p |
|---|---|---|---|---|---|---|---|---|---|
| Triac 0.8 mM | 0.72 | 0.82 | 0.84 | 0.76 | 0.82 | 0.079 | | | |
| Betamethasone 0.2 mM | 0.50 | 0.38 | 0.41 | 0.42 | 0.39 | 0.42 | 0.05 | 4 | |
| Bet. 0.2 mM + placebo cr. | 0.40 | 0.42 | 0.38 | 0.40 | 0.39 | 0.40 | 0.01 | 5 | |
| Bet. + TriAc cr. (0.01 % TriAc) | 0.50 | 0.52 | 0.45 | 0.53 | 0.50 | 0.50 | 0.03 | 5 | <0.05 |
| Bet. + TriAc cr. (0.03 %) | 0.50 | 0.55 | 0.60 | 0.56 | 0.57 | 0.56 | 0.04 | 5 | <0.05 |
| Bet. + 0.0008 mM KB-026 | 0.40 | 0.41 | 0.40 | 0.42 | 0.41 | 0.41 | 0.01 | 4 | |
| Bet. + 0.008 mM KB-026 | 0.45 | 0.42 | 0.46 | 0.44 | 0.45 | 0.44 | 0.01 | 4 | |
| Bet. + 0.08 mM KB-026 | 0.44 | 0.50 | 0.49 | 0.46 | 0.50 | 0.48 | 0.03 | 4 | |
| Bet. + 0.8 mM KB-026 | 0.50 | 0.52 | 0.48 | 0.51 | 0.50 | 0.50 | 0.01 | 4 | <0.05 |
| Bet. + 0.0008 mM TriProp | 0.41 | 0.40 | 0.46 | 0.40 | 0.41 | 0.42 | 0.03 | 4 | |
| Bet. + 0.008 mM TriProp | 0.45 | 0.50 | 0.40 | 0.42 | 0.48 | 0.45 | 0.04 | 4 | |
| Bet. + 0.08 mM TriProp | 0.50 | 0.48 | 0.47 | 0.50 | 0.44 | 0.48 | 0.02 | 4 | |
| Bet. + 0.8 mM TriProp | 0.50 | 0.45 | 0.47 | 0.48 | 0.52 | 0.48 | 0.03 | 4 | |
| Bet. + 0.0008 mM KB-067 | 0.42 | 0.39 | 0.40 | 0.39 | 0.40 | 0.40 | 0.01 | 4 | |
| Bet. + 0.008 mM KB-067 | 0.40 | 0.39 | 0.41 | 0.40 | 0.39 | 0.40 | 0.01 | 4 | |
| Bet. + 0.08 mM KB-067 | 0.40 | 0.40 | 0.41 | 0.39 | 0.41 | 0.40 | 0.01 | 4 | |
| Bet. + 0.8 mM KB-067 | 0.45 | 0.46 | 0.47 | 0.45 | 0.48 | 0.46 | 0.01 | 4 | |
| Vehicle (50% propanol/water) | 0.52 | 0.55 | 0.53 | 0.56 | 0.55 | 0.54 | 0.02 | 4 | <0.05 |

Figure 4:
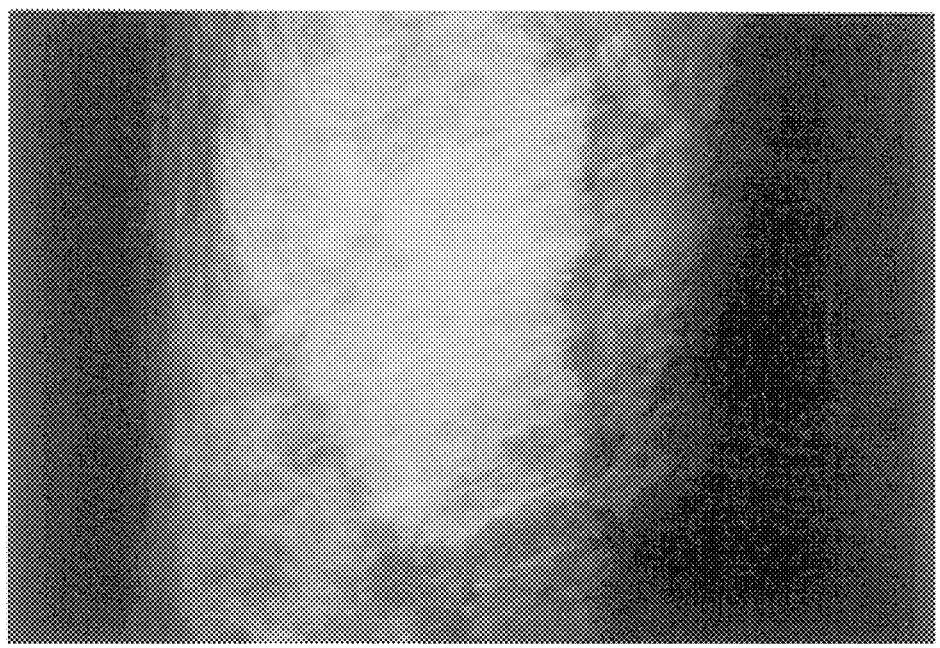
FIG. 4 is a photograph showing a volunteer's forearm extensor skin surface after 5 months of control cream-placebo formulation.

*p is defined as the probability that the result is due to chance alone.
"cr." = hydrophilic cream As shown in Table 3, all compounds were capable of preventing betamethasone-induced atrophy and thinning of the dermis. Each was effective at a slightly different concentration range. From the above tables, one can therefore receiving only a maintenance dose (5 mg) of prednisone. Multiple bruises covered each forearm extensor surface. Surface capillaries were visible through the skin and the forearms had a brown cast (FIG. 4).

A hydrophilic vanishing cream containing 30 mg of Triac per 100 ml vehicle alone was prepared as follows. Triac was added in 10 ml of 70% isopropanol per 120 ml vehicle and mixed to produce a 29 mg Triac per 100 ml cream. The cream was diluted with vehicle (a mixture of glyceryl stearate, safflower oil containing linoleic, oleic, palmitic, linolenic, and other fatty acid substituents, sorbitol, cetyl alcohol, stearic acid, triethanolamine) to produce the 10 mg/ml cream one part plus two parts vehicle, and subsequently diluted again in the same manner.

The above preparations were applied to the other forearm of the patient in a blinded fashion for a period of approximately six months. Due to the effects of the cream, patient blinding became impossible after approximately eight weeks. The following dose schedule was used in a consecutive manner: (1) Eight weeks of 30 mg Triac per 100 ml vehicle, followed by (2) 4 By weeks of 10 mg Triac per 100 ml vehicle, followed by (3) 12 weeks of 3.3 mg Triac per 100 ml vehicle.

At the 30 mg/ml, 5.6% isopropanol dose some pruritus occurred which was minor and did not prevent cream application. No pruritus occurred at the lowered dosages. During the treatment period, the patient had intermittent courses of prednisone ranging from 10 to 30 mg per day for periods up to two weeks.

Figure 5:
FIG. 5 is a photograph showing a volunteer's forearm extensor skin surface after 5 months of treatment with the composition of the invention.
Figure 6:
FIG. 6 is a photograph showing a volunteer's forearm volar forearm skin surface after five months of treatment with the composition of the invention.
Figure 7:
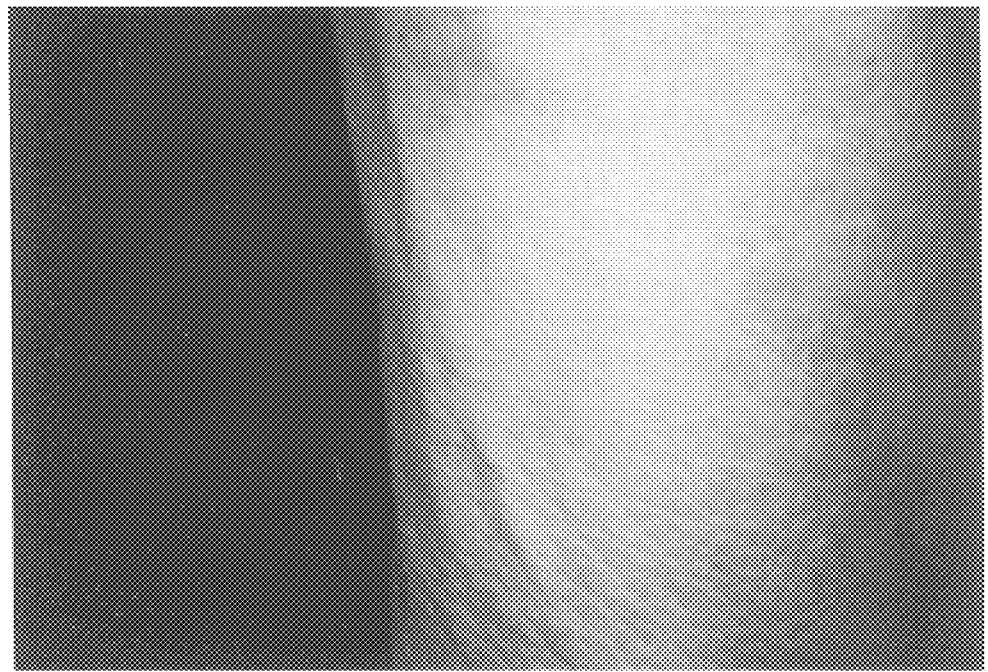
FIG. 7 is a photograph showing a volunteer's forearm volar forearm skin surface after 5 months of treatment with a control composition.
Figure 8:
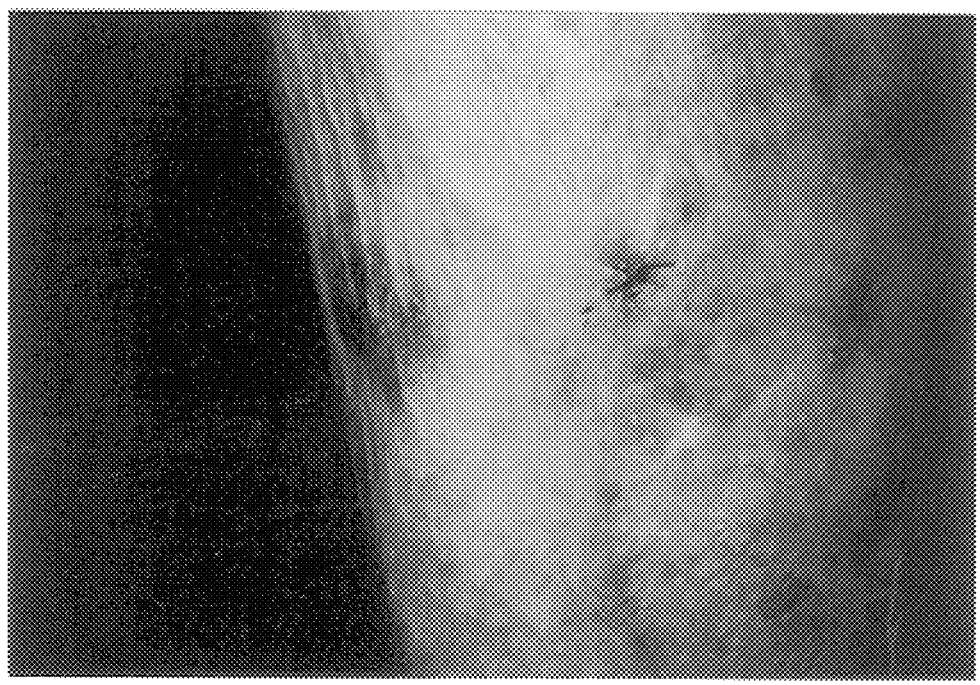
FIG. 8 is a photograph showing a volunteer's control extensor forearm and biopsy site.

Clinically, a change in the skin could be seen in eight weeks, and was remarked upon by untrained observers. Purpura (bruising) was markedly decreased in the treated arm (FIG. 5). After a total of six months of treatment, the patient was examined by a dermatologist. On blinded clinical examination, the treated arm (FIGS. 5, 6, and 9) appeared healthier with more even pigmentation, less brown cast, less wrinkling and slightly higher turgor and elasticity than the control arm (FIGS. 4, 7, and 8). Superficial veins were also more difficult to detect.

After six months of treatment, 3 mm punch biopsies were taken to identical depths. Biopsy of the extensor surface of the control forearm revealed solar elastosis, orthokeratosis, with epidermal and prominent dermal atrophy and reduced collagen. Biopsy of the extensor surface of the treated arm revealed no dermal atrophy and increased cellularity, and continued solar elastosis, orthokeratosis, and evidence for hyperkeratosis. Physically the treated specimen was thicker than the untreated one. Trichrome staining revealed an increase in collagen fibers in the reticular dermis in the treated specimen. Eccrine glands were situated far more superficially n in the untreated side.

Figure 9:
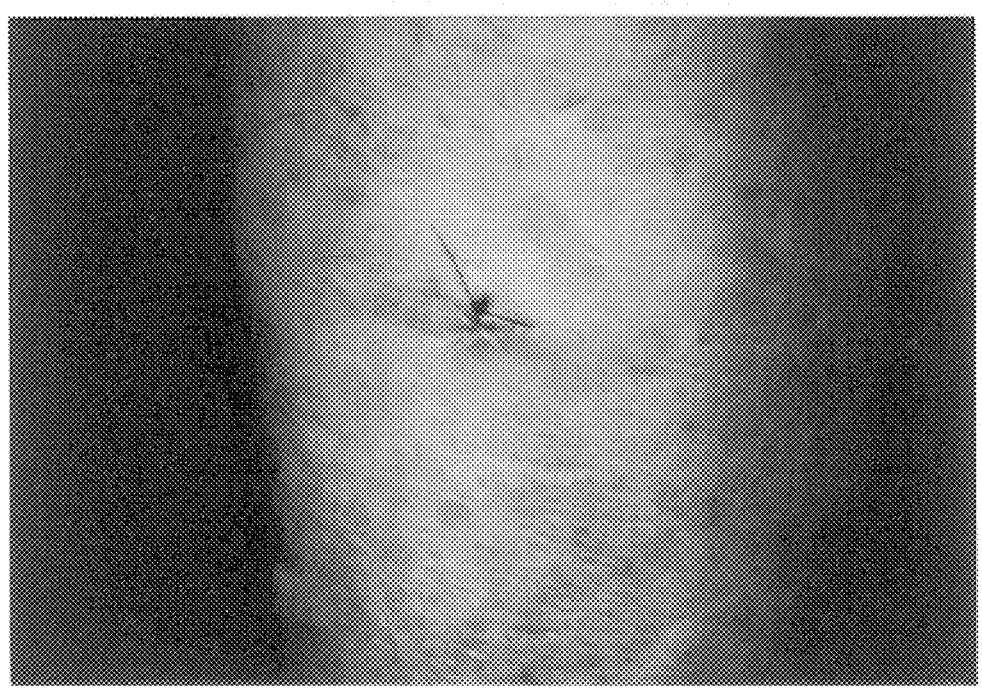
FIG. 9 is a photograph showing a volunteer's experimental extensor forearm and biopsy site.

After the biopsy, bruising around the biopsy occurred in the control forearm associated with the biopsy site and also with the bandage (FIG. 8). It did not develop in the treated arm (FIG. 9). The treated arm also has a greatly reduced purpuric response to injury and the biopsy site healed more readily (FIG. 9).

Skin thickness measurements were performed with a spring-loaded micrometer during skin tenting. The results are show in Table 4.

TABLE 4

Skin Thickness Measurements

| Site | Double Skin Measurement | Calculated Thickness |
|---|---|---|
| Treated Extensor Forearm | 2.16 mm | 1.08 mm |
| Untreated Extensor Forearm | 1.65 mm | 0.83 mm |

As shown in Table 4, double thickness skin measurements were taken from the extensor surface of each forearm, revealing a 0.25 mm single skin thickness difference in apparent skin thickness, or a 30% increase in the thickness of the skin.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A method for treating dermal atrophy of the skin, comprising the step of applying a composition to the skin of a mammal suffering from dermal atrophy of the skin, said composition comprising at least one thyroid hormone compound together with a pharmacologically acceptable base for topical application, wherein said thyroid hormone compound binds to TR-α or TR-β with an equilibrium dissociation constant, $K_d$, lower than 1 $\mu$M, wherein $$K_d=(R)\cdot(L)/(RL),$$

where (R) is the concentration of receptor, (L) is the concentration of ligand, and (RL) is the concentration of the receptor-ligand complex, and wherein said dermal atrophy of the skin is reduced.

2. The method of claim 1, wherein said composition comprises a concentration of $5\times10^8$ times $K_d$ or less of said at least one thyroid hormone compound.

3. The method of claim 1, wherein said at least one thyroid hormone compound is in chemically pure form.

4. The method of claim 1, wherein said pharmacologically acceptable base is selected from the group consisting of oil in water emulsions, water in oil emulsions, sprays, liposomes, creams, lotions, solutions, and combinations thereof.

5. The method of claim 1, wherein said pharmacologically acceptable base comprises one or more fatty acids, esters, or triglycerides selected from the group consisting of linoleic, oleic, palmitic, and linolenic fatty acids, esters, or triglycerides.

6. The method of claim 1, wherein said at least one thyroid hormone compound is at least partially dissolved in a solvent.

7. The method of claim 6, wherein said solvent is an organic solvent.

8. The method of claim 7, wherein said organic solvent comprises water and an alcohol.

9. The method of claim 8, wherein said alcohol is selected from the group consisting of isopropanol, ethanol, and combinations thereof.

10. The method of claim 1, wherein 100 ml of said composition comprises less than 200 mg of said thyroid hormone compound.

11. The method of claim 10, wherein 100 ml of said composition comprises less than 50 mg of said thyroid hormone compound.

12. A method of improving healing of wounded skin of a patient, comprising the step of applying a composition to the wounded skin of said patient, said composition comprising at least one thyroid hormone compound together with a pharmacologically acceptable base for topical application, wherein said thyroid hormone compound binds to TR-α or TR-β with an equilibrium dissociation constant, $K_d$, lower than 1 $\mu$m, wherein $$K_d=(R)\cdot(L)/(RL),$$

where (R) is the concentration of receptor, (L) is the concentration of ligand, and (RL) is the concentration of the receptor-ligand complex, and wherein said healing of said wounded skin is improved.

13. The method of claim 12, wherein said composition comprises at least one thyroid hormone compound selected from the group consisting of tri-iodothyroacetic acid, tri-iodopropionic acid, 4-(2,6-dibromo-4-(1H-tetrazol-5-ylmethyl)-phenoxy]-2-isopropyl-phenol, 4-(4-hydroxymethyl-2,6-diiodophenoxy)-2-iodo-phenol, and combinations thereof; and a pharmacologically acceptable base comprising oil in water emulsions, water in oil emulsions, sprays, liposomes, creams, lotions, solutions, and combinations thereof.

14. The method of claim 13, wherein 100 ml of said composition comprises less than 200 mg of said thyroid hormone compound.

15. The method of claim 14, wherein 100 ml of said composition comprises less than 50 mg of said thyroid hormone compound.

16. The method of claim 12, wherein said pharmacologically acceptable base further comprises one or more fatty acids, esters, or triglycerides selected from the group consisting of linoleic, oleic, palmitic, and linolenic fatty acids, esters, or triglycerides.

17. A method of dermatological surgical pretreatment of a patient with atrophied skin, comprising the step of applying a composition to the atrophied skin of said patient prior to dermatological surgery, said composition comprising at least one thyroid hormone compound together with a pharmacologically acceptable base for topical application, wherein said thyroid hormone compound binds to TR-α or TR-β with an equilibrium dissociation constant, $K_d$, lower than 1 μM, wherein $$K_d=(R)\cdot(L)/(RL),$$

where (R) is the concentration of receptor, (L) is the concentration of ligand, and (RL) is the concentration of the receptor-ligand complex.

18. The method of claim 17, wherein said composition comprises at least one thyroid hormone compound selected from the group consisting of tri-iodothyroacetic acid, tri-iodopropionic acid, 4-(2,6-dibromo-4-(1H-tetrazol-5-ylmethyl)-phenoxy]-2-isopropyl-phenol, 4-(4-hydroxymethyl-2,6-diiodophenoxy)-2-iodo-phenol, and combinations thereof; and a pharmacologically acceptable base comprising oil in water emulsions, water in oil emulsions, sprays, liposomes, creams, lotions, solutions, and combinations thereof.

19. The method of claim 18, wherein 100 ml of said composition comprises less than 200 mg of said thyroid hormone compound.

20. The method of claim 19, wherein 100 ml of said composition comprises less than 50 mg of said thyroid hormone compound.

21. The method of claim 17, wherein said pharmacologically acceptable base further comprises one or more fatty acids, esters, or triglycerides selected from the group consisting of linoleic, oleic, palmitic, and linolenic fatty acids, esters, or triglycerides.

22. The method of claim 1, wherein said at least one thyroid hormone compound selected from the group consisting of tri-iodothyronine; D and L thyroxine; 4-(2,6-dibromo-4-(1H-tetrazol-5-ylmethyl)-phenoxy)-2-isopropyl-phenol; 4-(4-hydroxymethyl-2,6-diiodophenoxy)-2-iodo-phenol; 3,3'5'tri-iodothyronine; 3,3'-diiodothyronine; 3,5,3',-Triiodo-L-thyronine methyl ester; 3,5,3'-triiodo-L-thyronine hydrochloride; L-thyroxine hydrochloride; 3-(4 (4-hydroxy-2 , 5-diiodophenoxy)-3,5-diiodophenyl) acetic acid; (4-(4-hydroxy-3-iodophenoxy)-3,5-diiodophenyl) acetic acid; tetraprop; (4-(4-hydroxy-3-iodophenoxy)-3,5-diiodophenyl)propionic acid; T4Bu; T3Bu; thyroxaminer triiodothyronamine; (5-benzyloxy-2-methoxyphenyl)-(2-methoxypyrimidin-5-yl)-methanol; benzyloxy-2-methoxyphenyl)-(6-methylpyridin-3-yl)methanol; (5-benzyloxy-2-methoxyphenyl)-(5-bromo-2-methoxypyridin-4-yl)methanol; (5-benzyloxy-2-methoxyphenyl)-(2,6-difluoropyridin-3-yl)methanol; (5-benzyloxy-2-methoxyphenyl)-(2-methoxypyridin-4-yl) methanol; 4-methoxy-3-((2-methoxypyrimidin-5-yl) methyl)phenol; 4-methoxy-3-((6-methylpyrid-3-yl)methyl) phenol; 5-benzyloxy-2-methoxybenzyl bromide; (5-benzyloxy-2-methoxyphenyl-(6-chloropyridazin-3-yl)-acetonitrile; 4-benzyloxy-2-(2-methoxythiazol-5-yl) methyl)anisole; 6-((5-hydroxy-2-methoxyphenyl)methyl) thiazol-2-(3H); 3'-heteroarylmethyl-4'-)-methyl-3,5-dinitro-N-trifluoro-acetyl-L-thyronine ethyl esters; 3'-heteroarylmethyl-3,5-di-iodo-4'-methyl-N-trifluoro-acetyl-L-thyronine ethyl esters; 3'-heteroarylmethyl analogues of 3,3',5-tri-iodo-L-thyronine; 3'-substituted derivatives of the thyroid hormone 3,3'5-triiodo-L-thyronine; L-3, 3'-T2; DL-Br2I; L-Br2iPr; L-Me2I; L-Me3; L-Me4; L-Me2IPr; DL-IMeI; L-3,5-Dimethyl-3'-isopropylthyronine; DL-BPT4; B-triac; BP-tetrac; DL-SBT3; DL-SBT4; DL-MBT3; MB-tetrac; T2F; T2Cl; T2Br; T2Me; T2Et; T2iPr; T2nPr; T2sBu; T2tBu; T2iBu; T2Phe; T2F2; T2Cl2; T2Me2; 3,5,3'-triiodo-D-thyronine; 3,5-diiodo-4-hydroxyphenylpropionic acid; aryloxamic acids; (arylamino)acetic acids; arylpropionic acids; arylthioacetic acids; (aryloxy)acetic acid; 3,3'-T2; 3,5-T2; 3',5'-T2; α-methyl-3,5,3'-triiodothyroacetic acid, α-methyl-3,5, 3'- triiodothyropropionic acid, and α-methyl-3,5,3',5,-tetraiodothyropropionic acid; methylene- and carbonyl-bridged analogs of iodinated thyronines or thyroacetic acids or iodinated benzofurans; 3,5-diiodo-4-(2-N,N-diethylaminoethoxy)phenyl-(2-butylbenzofur-3-yl) methanol hydrochloride; 2-n-butyl- 3-(3,5-diiodo-4-carboxymethoxy-benzoyl)benzofuran; 2-methyl-3-(3,5-diiodo-4-hydroxy-benzoyl)benzofuran; 2-methyl-3-(3,5-diiodo-4-carboxymethoxy-benzyl)benzofuran;) 4'-hydroxy-3'-iodo-3,5 diiodo-4-(2-N,N-dimethylamino-(ethoxy) benzophenone hydrochloride; 2-butyl-3-(3-iodo-4-hydroxybenzoyl) benzfuran; 4',4-dihydroxy 3'3, 5-triiodo-diphenylmethane; 3,5-diethyl,3'-isopropyl thyronine; and IpTA2 (3,5 diiodo-3'isopropyl thyroacetic acid) and pharmacologically acceptable salts and derivatives thereof.

* * * * *